United States Patent
Huboux et al.

(10) Patent No.: US 8,987,188 B2
(45) Date of Patent: Mar. 24, 2015

(54) BENZODIOXOLE DERIVATIVES AS WATERY ODORANTS

(75) Inventors: Alexandre Huboux, Geneva (CH); Jean-Marc Gaudin, Shanghai (CN); Pascal Millet, Geneva (CH); Fabrice Robvieux, Geneva (CH)

(73) Assignee: Firmenich SA, Geneva (CH)

( * ) Notice: Subject to any disclaimer, the term of this patent is extended or adjusted under 35 U.S.C. 154(b) by 162 days.

(21) Appl. No.: 13/876,404

(22) PCT Filed: Sep. 29, 2011

(86) PCT No.: PCT/EP2011/066951
§ 371 (c)(1),
(2), (4) Date: Mar. 27, 2013

(87) PCT Pub. No.: WO2012/045646
PCT Pub. Date: Apr. 12, 2012

(65) Prior Publication Data
US 2013/0288947 A1    Oct. 31, 2013

(30) Foreign Application Priority Data
Oct. 4, 2010    (EP) .................................... 10186421

(51) Int. Cl.
C11B 9/00 (2006.01)
C07D 317/46 (2006.01)
A61K 8/49 (2006.01)
A61Q 13/00 (2006.01)

(52) U.S. Cl.
CPC .............. *C07D 317/46* (2013.01); *A61K 8/498* (2013.01); *A61Q 13/00* (2013.01); *C11B 9/0076* (2013.01)
USPC .......................................................... 512/12

(58) Field of Classification Search
USPC .......................................................... 512/12
See application file for complete search history.

(56) References Cited

U.S. PATENT DOCUMENTS

| 3,584,002 A | 6/1971 | Williams |
| 3,799,892 A | 3/1974 | Berreboom et al. |
| 5,990,076 A | 11/1999 | Gaudin et al. |

FOREIGN PATENT DOCUMENTS

| EP | 1 136 481 | 11/2002 |
| EP | 902 024 | 3/2003 |
| EP | 902024 | 3/2003 |
| JP | 2002-068908 | 3/2002 |

OTHER PUBLICATIONS

Adam, et al. Journal of the American Chemical Society, "Thermal and Bromide Ion-Catalyzed Rearrangement of Benzofuran Dioxetanes to 1-Oxaspiro[2.5]octa-5,7-dien-4-ones", vol. 116, No. 15, 1994.*
International Search Report and Written Opinion, application n° PCT/EP2011/066951, mailed Jan. 19, 2012.
Adam et al., Journal of the American Chemical Society, 116:6713-6718 (1994).
Adam et al., Journal of the American Chemical Society,113:8005-8011 (1991).
Baines et al., J. Med. Chem., ( 965) 8:81-90.
Turner et al., J. Agric. Food Chem., (2002), 50:4554-4566.

* cited by examiner

*Primary Examiner* — Ling Choi
*Assistant Examiner* — Lanee Reuther
(74) *Attorney, Agent, or Firm* — Winston & Strawn LLP

(57) ABSTRACT

The present invention relates to compounds of formula (I) in the form of any one of its stereoisomers or a mixture thereof, and wherein $R^1$ represents a substituent of the benzene ring and is a bromine atom or a linear, branched or cyclic $C_{1-8}$ alkyl, alkenyl, alkoxy or alkenyloxy group; $R^2$ represents a $C_{1-3}$ alkyl group; and $R^3$ represents a hydrogen atom or a methyl or ethyl group; and their use as perfuming ingredients, for instance to impart odor notes of the watery/ozone type.

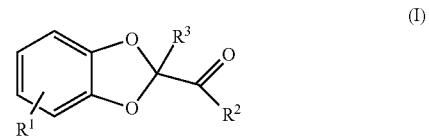

(I)

19 Claims, No Drawings

BENZODIOXOLE DERIVATIVES AS WATERY ODORANTS

TECHNICAL FIELD

The present invention relates to the field of perfumery. More particularly, it concerns a new class of benzodioxole derivatives which are particularly useful as perfuming ingredients. Therefore, following what is mentioned herein, the present invention comprises also the invention's compounds as part of a perfuming composition or of a perfuming consumer product.

PRIOR ART

To the best of our knowledge, the compounds responding to formula (I) herein below are all new chemicals, with the exception of 1-[5-(1,1-dimethylethyl)-2-methyl-1,3-benzodioxol-2-yl]-ethanone (see J.A.C.S. 1994, 116, 6713, described as simple chemical compound), 1-(4-methoxy-2-methyl-1,3-benzodioxol-2-yl)-ethanone (see J.A.C.S. 1991, 113, 8005, described as simple chemical compound) and 1-(5-methoxy-2-methyl-1,3-benzodioxol-2-yl)-ethanone (see J.A.C.S. 1994, 116, 6713, described as simple chemical compound). However none of the prior art disclosures concerning such compounds suggests or anticipates the organoleptic properties, and their usefulness, of the compounds of formula (I).

To the best of our knowledge, the closest analogues known in the perfumery and belonging to the same broad olfactive family are 2H,4H-1,5-benzodioxepin-3-one derivatives (see for examples U.S. Pat. No. 3,584,002 or 3,799,892 or EP 902024 or 1136481) which have anyway a quite different structure. Once again, these prior art documents do not report or suggest any organoleptic properties of the compounds of formula (I), or any use of said compounds in the field of perfumery.

Now odorant chemicals providing odor notes of the watery/ozone type are extremely rare and of very high interest for the perfumery art. There is therefore a need for new watery odorants providing an increased palette of odor tonalities.

DESCRIPTION OF THE INVENTION

We have now surprisingly discovered that a compound of formula

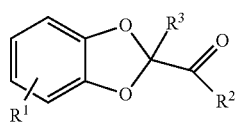

(I)

in the form of any one of its stereoisomers or a mixture thereof, and wherein $R^1$ represents a substituent of the benzene ring and is a halogen atom or a linear, branched or cyclic $C_{1-8}$ alkyl, alkenyl, alkynyl, alkoxy or alkenyloxy group;
$R^2$ represents a $C_{1-3}$ alkyl group; and
$R^3$ represents a hydrogen atom or a methyl or ethyl group;
can be used as perfuming ingredient, for instance to impart odor notes of the watery/ozone type.

For the sake of clarity, by the expression "$R^1$ represents a substituent of the benzene ring", or the similar, it is meant the normal meaning understood by a person skilled in the art, i.e. that said group can be bound to the benzene ring at any one of the available positions, i.e. in the ortho or meta position of an oxygen atom or the benzodioxole moiety. For the sake of clarity, by the expression "linear, branched or cyclic" it is meant that said $R^1$ can be in the form of, e.g., a linear group or can also be in the form of a mixture of said type of topologies, e.g. a specific $R^1$ may comprise a linear moiety and a cyclic moiety, unless a specific limitation to only one type is mentioned.

According to any one of the above embodiments of the invention, said compounds (I) are of formula

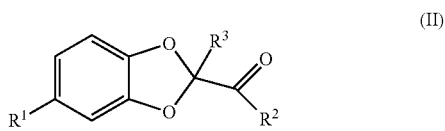

(II)

wherein $R^1$, $R^2$ and $R^3$ are as defined in formula (I).

According to any one of the above embodiments of the invention, said compounds (I) or (II) are those wherein $R^1$ represents a substituent of the benzene ring and is a bromine atom or a linear, branched or cyclic $C_{1-6}$ alkyl, alkenyl, alkynyl, alkoxy or alkenyloxy group.

According to any one of the above embodiments of the invention, said compounds (I) or (II) are those wherein $R^1$ represents a substituent of the benzene ring and is a linear or branched $C_{1-6}$ alkyl, alkenyl, alkynyl or alkoxy group or represents a $C_{5-6}$ cyclic alkyl, alkenyl or methylcyloalkyl (i.e. $CH_2$-cycloalkyl) group.

According to any one of the above embodiments of the invention, said compounds (I) or (II) are those wherein $R^1$ represents a substituent of the benzene ring and is a linear or branched $C_{1-6}$ alkyl or alkenyl group or represents a $C_{5-6}$ cyclic alkyl, alkenyl or methylcyloalkyl (i.e. $CH_2$-cycloalkyl) group.

According to any one of the above embodiments of the invention, said compounds (I) or (II) are those wherein $R^1$ represents a substituent of the benzene ring and is a linear or branched $C_{1-6}$ alkyl, alkenyl, alkoxy or alkenyloxy group.

According to any one of the above embodiments of the invention, said compounds (I) or (II) are those wherein $R^1$ represents a substituent of the benzene ring and is a linear or branched $C_{1-6}$ alkyl or alkenyl group. Alternatively said $R^1$ represents a linear or branched $C_{3-6}$ alkyl or alkenyl group. Non-limiting examples of such $R^1$ group are propyl, iso-propyl, tert-butyl, iso-butyl, sec-butyl, n-butyl, n-pentyl, iso-pentyl, tert-pentyl or n-hexyl or prop-1-enyl or hex-2-enyl.

According to any one of the above embodiments of the invention, said compounds (I) are those wherein $R^2$ represents a methyl or ethyl group. In particular $R^2$ represents a methyl group.

According to any one of the above embodiments of the invention, said compounds (I) are those wherein $R^3$ represents a hydrogen atom or a methyl group.

According to any one of the above embodiments of the invention, said compounds (I) are $C_{10}$-$C_{15}$ compounds, or even are $C_{12}$-$C_{14}$ compounds.

The compounds of formula (I) are all new compounds and are therefore another object of the present invention, except 1-[5-(1,1-dimethylethyl)-2-methyl-1,3-benzodioxol-2-yl]-ethanone, 1-(4-methoxy-2-methyl-1,3-benzodioxol-2-yl)-ethanone and 1-(5-methoxy-2-methyl-1,3-benzodioxol-2-yl)-ethanone as described above.

As specific example of the invention's compounds, one may cite, as non-limiting example, 1-(5-isopropylbenzo[d][1,3]dioxol-2-yl) ethanone which possesses an odor having a watery/ozonic note and a floral note, of the lily of the valley-anisic type. The combination of watery and floral notes is quite unusual in the art of perfumery and renders said compound all the more interesting. When said compound is compared to its closest analogue in the 2H,4H-1,5-benzodioxepin-3-one family, namely 7-isopropyl-2H,4H-1,5-benzodioxepin-3-one, the present invention's compound distinguishes itself by the presence of said floral note, absent in the prior art compound.

As other example, one may cite 1-(5-propyl-1,3-benzodioxol-2-yl)-1-ethanone which, as the compound above, possesses also a mix of a watery/ozonic note and a fresh green floral (lily of the valley) note. However said compound also has an aldehydic note. The odor of said compound reminds of a mix of cyclosal (Artcander N° 758, known as floral ingredient) and 3-(3-isopropyl-1-phenyebutanal (known as watery ingredient). When said compound is compared to its closest analogue in the 2H,4H-1,5-benzodioxepin-3-one family, namely 7-propyl-2H,4H-1,5-benzodioxepin-3-one, the present invention's compound distinguishes itself by the presence of said floral note, absent in the prior art compound.

As further example, one may cite 1-(5-pentylbenzo[d][1,3]dioxol-2-yl)ethanone which possesses a very powerful and extremely substantive odor having an unusual ozonic and balsamic duality. The odor is a mix of ozonic, cucumber type notes and balsamic, cinnamic notes with also an aldehydic aspect. When said compound is compared to its closest analogue in the 2H,4H-1,5-benzodioxepin-3-one family, namely 7-pentyl-2H,4H-1,5-benzodioxepin-3-one, the present invention's compound distinguishes itself by the presence of said balsamic note, absent in the prior art compound.

As other specific, but non-limiting, examples of the invention's compounds, one may cite the following ones in Table 1:

TABLE 1

Invention's compounds and their odor properties

| Compound structure and name | Odor notes |
|---|---|
| 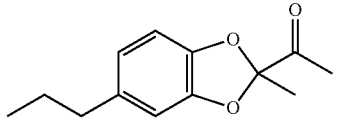<br>1-(2-methyl-5-propylbenzo[d][1,3]dioxol-2-yl)ethanone | Marine, ozone, oyster and aldehydic notes |
| 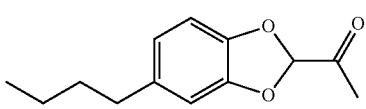<br>1-(5-butylbenzo[d][1,3]dioxol-2-yl)ethanone | A very clean ozonic, watermelon note with a fatty aspect. Olfactively between 1-(5-pentylbenzo[d][1,3]dioxol-2-yl)ethanone described above and 1-(5-cyclopentylbenzo[d][1,3]dioxol-2-yl)ethanone described below |
| 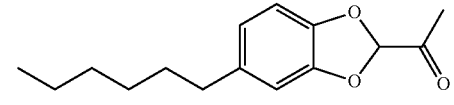<br>1-(5-hexylbenzo[d][1,3]dioxol-2-yl)ethanone | Ozonic, milky, aldehydes notes |
| 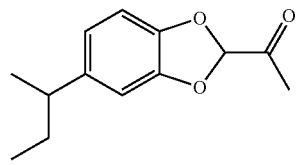<br>1-(5-sec-butylbenzo[d][1,3]dioxol-2-yl)ethanone | Ozonic and floral notes |
| 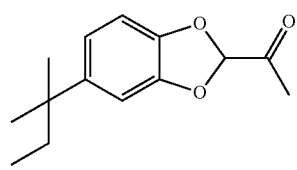<br>1-(5-tert-pentylbenzo[d][1,3]dioxol-2-yl)ethanone | Watery, sweet-floral and slightly fatty notes |

TABLE 1-continued

Invention's compounds and their odor properties

| Compound structure and name | Odor notes |
|---|---|
| 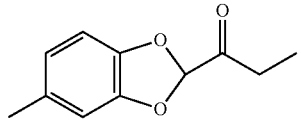 1-(5-methylbenzo[d][1,3]dioxol-2-yl)propan-1-one | Watery and floral notes |
| 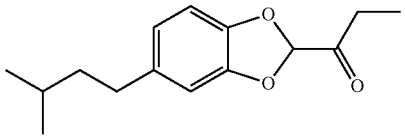 1-(5-isopentylbenzo[d][1,3]dioxol-2-yl)propan-1-one | Watery and milky notes |
| 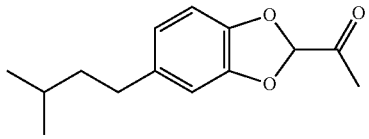 1-(5-isopentylbenzo[d][1,3]dioxol-2-yl)ethanone | Ozone and fatty notes |
| 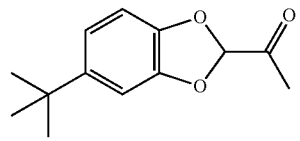 1-(5-tert-butyl-1,3-benzodioxol-2-yl)-1-ethanone | Multiodorant, of the mellony, marine-salty, ozonic type and possesses also a clean fatty/aldehydic aspect |
| 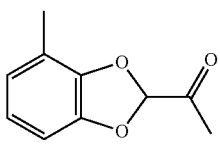 1-(4-methyl-1,3-benzodioxol-2-yl)-1-ethanone | Watery, seeweed, crab, typically marine watery, with a floral undernote |
| 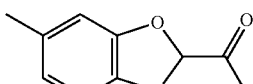 1-(5-methyl-1,3-benzodioxol-2-yl)-1-ethanone | Watery, milky notes |
| 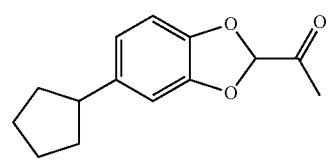 1-(5-cyclopentylbenzo[d][1,3]dioxol-2-yl)ethanone | Ozonic - lactonic duality, fruity/peachy notes. Such duality is unique in the palette of the perfumer |

TABLE 1-continued

Invention's compounds and their odor properties

| Compound structure and name | Odor notes |
|---|---|
| 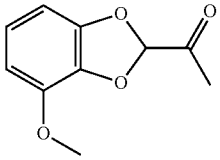<br>1-(4-methoxybenzo[d][1,3]dioxol-2-yl)ethanone | Ozone, marine, lactonic notes |
| 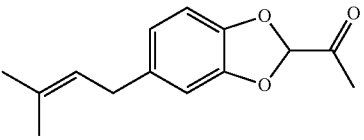<br>1-(5-(3-methylbut-2-enyl)benzo[d][1,3]dioxol-2-yl)ethanone | Watery, ozone, floral, aldehyde notes |
| 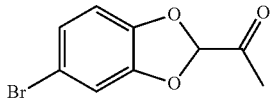<br>1-(5-bromobenzo[d][1,3]dioxol-2-yl)ethanone | Oyster, watery, see notes |
| 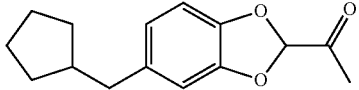<br>1-(5-(cyclopentylmethyl)benzo[d][1,3]dioxol-2-yl)ethanone | Ozonic, lactonic, aldehydic, fatty notes |
| 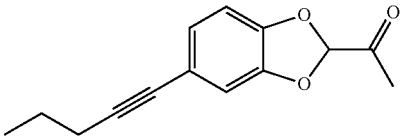<br>1-(5-(pent-1-ynyl)benzo[d][1,3]dioxol-2-yl)ethanone | Ozonic, seaweed, watery notes |
| 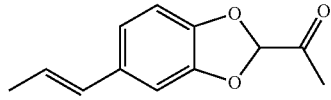<br>(E)-1-(5-(prop-1-enyl)benzo[d][1,3]dioxol-2-yl)ethanone | Watery, fishy, slightly milky, fatty notes |
| 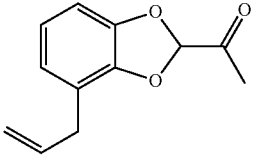<br>1-(4-allylbenzo[d][1,3]dioxol-2-yl)ethanone | Ozonic, seeweed notes |

TABLE 1-continued

Invention's compounds and their odor properties

| Compound structure and name | Odor notes |
|---|---|
| 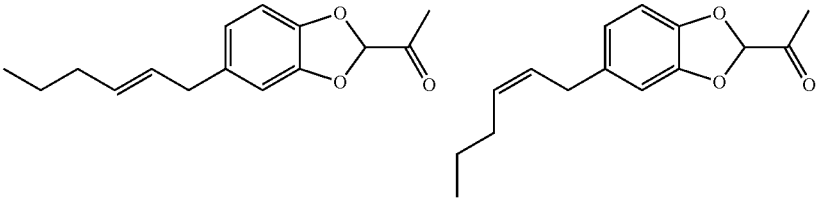<br>(E/Z)-1-(5-(hex-2-enyl)benzo[d][1,3]dioxol-2-yl)ethanone | Watery, oyster, ozonic, aldehyde, slightly fatty notes |

As can be noticed by the above odor descriptions, the invention's compounds, in addition to the watery/ozone notes, have also notes or aspect of floral, balsamic and/or fatty-aldehyde types.

According to a particular embodiment of the invention, the compounds of formula (I) are 1-(5-isopropylbenzo[d][1,3]dioxol-2-yl)ethanone, 1-(5-propyl-1,3-benzodioxol-2-yl)-1-ethanone, 1-(5-pentylbenzo[d][1,3]dioxol-2-yl)ethanone, 1-(2-methyl-5-propylbenzo[d][1,3]dioxol-2-yl)ethanone, 1-(5-butylbenzo[d][1,3]dioxol-2-yl)ethanone, 1-(5-hexylbenzo[d][1,3]dioxol-2-yeethanone, 1-(5-tert-pentylbenzo[d][1,3]dioxol-2-yl)ethanone, 1-(5-tert-butyl-1,3-benzodioxol-2-yl)-1-ethanone, 1-(5-cyclopentylbenzo[d][1,3]dioxol-2-yl)ethanone, 1-(5-(3-methylbut-2-enyl)benzo[d][1,3]dioxol-2-yl)ethanone, 1-(5-(cyclopentylmethyl)benzo[d][1,3]dioxol-2-yl)ethanone, (E)-1-(5-(prop-1-enyl)benzo[d][1,3]dioxol-2-yl)ethanone, (E/Z)-1-(5-(hex-2-enyl)benzo[d][1,3]dioxol-2-yl)ethanone or 1-(4-methyl-1,3-benzodioxol-2-yl)-1-ethanone.

In particular such compounds are 1-(5-isopropylbenzo[d][1,3]dioxol-2-yl) ethanone, 1-(5-propyl-1,3-benzodioxol-2-yl)-1-ethanone, 1-(5-pentylbenzo[d][1,3]dioxol-2-yl)ethanone, 1-(2-methyl-5-propylbenzo[d][1,3]dioxol-2-yl) ethanone, (E)-1-(5-(prop-1-enyl)benzo[d][1,3]dioxol-2-yl) ethanone, (E/Z)-1-(5-(hex-2-enyl)benzo[d][1,3]dioxol-2-yl) ethanone or 1-(5-butylbenzo[d][1,3]dioxol-2-yl) ethanone.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting example, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not of formula (I). Moreover, by "perfuming co-ingredient" it is meant here a compound which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modern perfumery, i.e. fine or functional perfumery, to positively impart or modify the odor of a consumer product into which said compound (I) is added. Consequently, a perfuming consumer product which comprises:
i) as perfuming ingredient, at least one compound of formula (I), as defined above; and
ii) a perfumery consumer base;
is also an object of the present invention.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer bases can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.05% to 10% by weight, or even more, of the compounds of the invention based on the weight of the composition into which they are incorporated. Concentrations lower than these, such as in the order of 0.01% to 5% by weight, can be used when these compounds are incorporated into perfumed articles, percentage being relative to the weight of the article.

The invention's compounds can be prepared according to a method as described in the examples and summarized in Scheme 1 herein below:

Scheme 1: Synthetic approach to the compounds of formula (I)

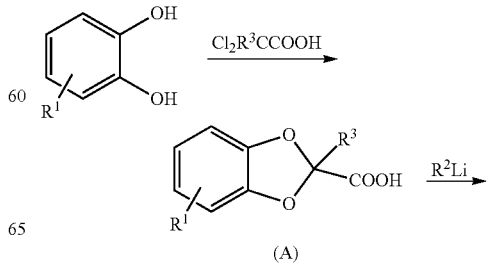

(A)

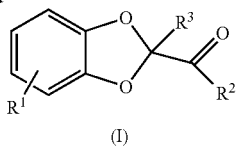

(I)

wherein R¹, R² and R³ have the same meaning as provided in formula (I).

The carboxylic acid intermediates (A) are also new compounds with the exception of 4-methoxy-1,3-benzodioxole-2-carboxylic acid (see JP 2002068908—agrochemical compounds), 5-methyl-1,3-benzodioxole-2-carboxylic acid (see J. Med. Chem., 1965, 8, 81) and 4-methyl-1,3-benzodioxole-2-carboxylic acid (see J. Agric. & Food Chem., 2002, 50, 4554), and are also another object of the present invention as intermediate for the preparation of useful chemicals. Particular carboxylic acid are those required for the preparation of the chemicals of formula (I) above cited specifically.

EXAMPLES

The invention will now be described in further detail by way of the following examples, wherein the abbreviations have the usual meaning in the art, the temperatures are indicated in degrees centigrade (° C.); the NMR spectral data were recorded in CDCl₃ (if not stated otherwise) with a 360 or 400 MHz machine for ¹H and ¹³C, the chemical shifts δ are indicated in ppm with respect to TMS as standard, the coupling constants J are expressed in Hz.

Example 1

Synthesis of Compounds of Formula (I)

1-(5-propyl-1,3-benzodioxol-2-yl)-1-ethanone

First Step—A suspension of potassium carbonate (69.1 g, 0.500 mol), 4-propylcatechol (30.44 g, 0.200 mol) and potassium iodide (4.98 g, 0.0300 mol) in 150 ml of isobutanol was heated at reflux while dichloroacetic acid (25.8 g, 0.200 mol) was added in 5 minutes. A further quantity of acid (2.6 g, 0.020 mol) was added in 1 minute after 3 hours at reflux and the reaction mixture cooled to room temperature after a total of 4.5 minutes. 100 ml of methanol was added and the dark brown suspension was filtered. The solids were washed with a total of 200 ml of methanol and the crude product concentrated. The resulting brown solid was taken up in 200 ml of water and extracted with three 100 ml portions of ether. 100 ml of ether was added to the aqueous phase and this mixture was acidified while stirring to pH 2. The two layers were separated and the aqueous phase extracted with 100 ml of ether. The two ethereal phases were combined, washed with 50 ml of water and 50 ml of brine and dried over MgSO₄. Filtration and concentration gave 35.5 g of an oil. This oil was purified by vacuum distillation (115-138° C., 0.4 mbar) through a short path to give a solid which was recrystallised from 110 ml of heptane to give 16.23 g (39%) of the carboxylic acid.

Second Step—A solution of the carboxylic acid (13.19 g, 63.35 mmol) in 350 ml of THF was cooled to 0° C. while a solution of methyl lithium (97 ml of a 1.6 M solution, 155 mmol) was added in 5 minutes (alternatively, the lithium salt is formed by heating with 1 equivalent of lithium hydroxide suspension in refluxing toluene and some THF and 1 equivalent of methyl lithium is added to the resulting salt). The reaction mixture was stirred below 0° C. for an additional 40 minutes and was then transferred in about 5 minutes, via a cannula, to a flask containing a rapidly stirring mixture of HCl (17 g, 0.17 mol) in 500 ml of water. 150 g of sodium chloride was added with stirring followed by 200 ml of heptane and the two layers were separated. The aqueous phase was extracted with two 100 ml portions of heptane and the combined organic phases washed with 100 ml of saturated sodium bicarbonate solution, 100 ml of brine and then dried with K₂CO₃. Filtration and concentration gave 12.35 g of a brown oil which was purified by flash chromatography on silica gel (elution with 4-2% toluene/2-4% ethyl acetate/heptane followed by 6-8% ethyl acetate/heptane) to give 9.53 g of a colorless oil. This oil was further purified by vacuum distillation (125° C., 1.5 mbar) in a Kugelrohr oven to give 8.87 g (68%) of a colorless oil.

¹H-NMR: 0.92 (t, J=7, 3H); 1.53-1.66 (m, 2H); 2.28 (s, 3H); 2.51 (t, J=7, 2H); 6.00 (s, 1H); 6.67 (dd, J=7, 1, 1H); 6.72 (d, J=1, 1H); 6.77 (d, J=7, 1H).

¹³C-NMR: 13.7 (q), 24.1 (q), 24.7 (t), 37.7 (t), 106.6 (d), 108.3 (d), 109.2 (d), 121.8 (d), 137.4 (s), 144.7 (s), 146.7 (s), 200.6 (d).

1-(5-tert-butyl-1,3-benzodioxol-2-yl)-1-ethanone

Obtained in 54% (1ˢᵗ step) and 27% (2ⁿᵈ step) yields from 4-tert-butylcatechol according to the typical procedure described for 1-(5-propyl-1,3-benzodioxol-2-yl)-1-ethanone.

¹H-NMR: 1.28 (s, 9H); 2.29 (s, 3H); 6.00 (s, 1H); 6.78 (d, J=8, 1H); 6.88 (dd, J=8, 2, 1H); 6.94 (d, J=2, 1H).

¹³C-NMR: 24.1 (q), 31.6 (3q), 34.7 (s), 106.6 (2d), 107.9 (d), 118.6 (d), 144.3 (s), 146.1 (s), 146.7 (s), 200.4 (d).

1-(5-isopropylbenzo[d][1,3]-dioxol-2-yl)ethanone

Obtained in 47% (1ˢᵗ step) and 30% (2ⁿᵈ step) yields from 4-isopropylcatechol according to the typical procedure described for 1-(5-propyl-1,3-benzodioxol-2-yl)-1-ethanone.

¹H-NMR: 1.21 (d, J=6.9, 6H); 2.28 (s, 3H); 2.80-2.88 (m, 1H); 5.98 (s, 1H); 6.71 (dd, J=8, 1.8, 1H); 6.77 (d, J=8, 1H); 6.77 (d, J=1.8, 1H).

¹³C NMR: 24.1 (q), 24.2 (q, 2C), 33.9 (d), 106.6 (d), 107.2 (d), 108.3 (d), 119.8 (d), 143.8 (s), 144.6 (s), 146.8 (s), 200.5 (s).

1-(5-pentylbenzo[d][1,3]-dioxol-2-yl)ethanone

Obtained in 38% (1ˢᵗ step) and 16% (2ⁿᵈ step) yields from 4-pentylcatechol according to the typical procedure described for 1-(5-propyl-1,3-benzodioxol-2-yl)-1-ethanone.

¹H-NMR: 0.89 (t, J=7.2, 3H); 1.25-1.36 (m, 4H); 1.53-1.60 (m, 2H); 2.27 (s, 3H); 2.52 (t, J=7.7, 2H); 6.00 (s, 1H); 6.66 (dd, J=8, 1, 1H); 6.71 (d, J=1.6, 1 H); 6.76 (d, J=7.8, 1H).

¹³C NMR: 14.0 (q), 22.5 (t), 24.0 (q), 31.4 (t), 31.4 (t), 35.6 (t), 106.6 (d), 108.3 (d), 109.1 (d), 121.7 (d), 137.6 (s), 144.7 (s), 146.7 (s), 200.4 (s).

1-(5-isopentylbenzo[1,3]-dioxol-2-yl)ethanone

Obtained in 40% (1ˢᵗ step) and 36% (2ⁿᵈ step) yields from 4-(3-methylbutyl)-catechol according to the typical procedure described for 1-(5-propyl-1,3-benzodioxol-2-yl)-1-ethanone.

¹H-NMR: 0.92 (d, J=6.5, 6H); 1.41-1.48 (m, 2H); 1.51-1.60 (m, 1H); 2.27 (s, 3H); 2.48-2.55 (m, 3H); 6.00 (s, 1H); 6.58-6.7 (m, 2H); 7.72 (d, J=1.7, 1H); 6.76 (d, J=8.2, 1H).
¹³C NMR: 22.5 (q), 24.0 (q), 27.5 (d), 33.5 (t), 41.0 (t), 106.5 (d), 108.3 (d), 109.1 (d), 121.6 (d), 137.7 (s), 144.6 (s), 146.7 (s), 200.4 (s).

1-(5-methylbenzo[d][1,3]-dioxol-2-yl)propan-1-one

Obtained in 30% (1$^{st}$ step) and 33% (2$^{nd}$ step) yields from 4-methylcatechol according to the typical procedure described for 1-(5-propyl-1,3-benzodioxol-2-yl)-1-ethanone, except the use of ethyl lithium instead of methyl lithium.
¹H-NMR: 1.08 (t, J=7.2, 3H); 2.27 (s, 3H); 2.65 (q, J=7.2, 2H); 6.02 (s, 1H); 6.65 (d, J=7.8, 1H); 6.69 (s, 1H); 6.73 (d, J=7.8, 1H).
¹³C NMR: 6.6 (q), 21.1 (q), 30.0 (t), 106.5 (d), 108.3 (d), 109.8 (d), 122.2 (d), 132.2 (s), 144.6 (s), 146.8 (s), 203.3 (s).

1-(5-isopentylbenzo[d][1,1]-dioxol-2-yl)propan-1-one

Obtained in 40% (1$^{st}$ step) and 25% (2$^{nd}$ step) yields from 4-(3-methylbutyl)-catechol according to the typical procedure described for 1-(5-propyl-1,3-benzodioxol-2-yl)-1-ethanone, except the use of ethyl lithium instead of methyl lithium.
¹H-NMR: 0.92 (d, J=6.8, 6H); 1.09 (t, J=7.2, 3H); 1.42-1.48 (m, 2H); 1.51-1.60 (m, 1H); 2.53 (m, 2H); 2.66 (q, J=7.2, 2H); 6.02 (s, 1H); 6.66 (dd, J=8, 1.8, 1H); 6.71 (d, J=1.8, 1H); 6.75 (d, J=8, 1H).
¹³C NMR: 22.5 (q, 2C), 24.0 (q), 27.6 (d), 30.0 (t), 33.5 (t), 41.0 (t), 106.6 (d), 108.3 (d), 109.0 (d), 121.6 (d), 137.7 (s), 144.7 (s), 146.8 (s), 203.3 (s).

1-(2-methyl-5-propylbenzo[d][1,3]-dioxol-2-yl)ethanone

Obtained in 65% (1$^{st}$ step) and 12% (2$^{nd}$ step) yields from 4-propyl-catechol according to the typical procedure described for (1), except the use of 2,2-dichloropropanoic acid instead of dichloroacetic acid.
¹H-NMR: 0.92 (t, J=7.4, 3H); 1.54-1.64 (m, 2H); 1.71 (s, 3H); 2.26 (s, 3H); 2.5 (t, J=7.5, 2H); 6.64 (dd, J=8, 1.7, 1H); 6.67 (d, J=1.7, 1H); 6.72 (d, J=8, 1H).
¹³C NMR: 13.7 (q), 20.2 (q), 24.1 (q), 24.8 (t), 37.8 (t), 108.2 (d), 109.1 (d), 113.7 (s), 121.5 (d), 137.0 (s), 144.8 (s), 146.8 (s), 201.7 (s).

1-(5-butylbenzo[d][1,3]-dioxol-2-yl)ethanone

Obtained in 58% (1$^{st}$ step) and 27% (2$^{nd}$ step) yields from 4-butylcatechol according to the typical procedure described for 1-(5-propyl-1,3-benzodioxol-2-yl)-1-ethanone.
¹H-NMR: 0.92 (t, J=7.3, 3H); 1.28-1.38 (m, 2H); 1.51-1.58 (m, 2H); 2.27 (s, 3H); 2.53 (t, J=7.7, 2H); 5.99 (s, 1H); 6.66 (dd, J=7.9, 1.7, 1H); 6.71 (d, J=1.7, 1H); 6.76 (d, J=7.9, 1H).
¹³C NMR: 13.9 (q), 22.2 (t), 24.0 (q), 33.8 (t), 35.4 (t), 106.6 (d), 108.3 (d), 109.1 (d), 121.7 (d), 137.6 (s), 144.7 (s), 146.7 (s), 200.4 (s).

1-(5-hexylbenzo[d][1,3]-dioxol-2-yl)ethanone

Obtained in 92% (1$^{st}$ step) and 20% (2$^{nd}$ step) yields from 4-hexylcatechol according to the typical procedure described for 1-(5-propyl-1,3-benzodioxol-2-yl)-1-ethanone.
¹H-NMR: 0.87 (t, J=6.9, 3H); 1.26-1.33 (m, 6H); 1.51-1.59 (m, 2H); 2.27 (s, 3H); 2.52 (t, J=7.7, 2H); 5.99 (s, 1H); 6.66 (dd, J=8, 1.6, 1H); 6.71 (d, J=1.6, 1H); 6.75 (d, J=8, 1H).
¹³C NMR: 14.1 (q), 22.6 (t), 24.0 (q), 28.9 (t), 31.7 (t), 31.7 (t), 35.7 (t), 106.6 (d), 108.3 (d), 109.1 (d), 121.7 (d), 137.6 (s), 144.6 (s), 146.7 (s), 200.4 (s).

1-(5-sec-butylbenzo[d][1,3]-dioxol-2-yl)ethanone

Obtained in 69% (1$^{st}$ step) and 30% (2$^{nd}$ step) yields from 4-sec-butylcatechol according to the typical procedure described for 1-(5-propyl-1,3-benzodioxol-2-yl)-1-ethanone.
¹H-NMR: 0.81 (t, J=7.3, 3H); 1.19 (d, J=7.0, 3H); 1.49-1.58 (m, 2H); 2.29 (s, 3H); 2.5-2.56 (m, 1H); 6.00 (s, 1H); 6.67 (dd, J=8, 1.4, 1H); 6.72 (d, J=1.4, 1H); 6.77 (d, J=8, 1H).
¹³C NMR: 12.2 (q), 22.0 (q), 24.1 (q), 31.3 (t), 41.5 (d), 106.6 (d), 107.6 (d), 108.3 (d), 120.6 (d), 142.5 (s), 144.7 (s), 146.8 (s), 200.5 (s).

1-(5-tert-pentylbenzo[d][1,3]-dioxol-2-yl)ethanone

Obtained in 70% (1$^{st}$ step) and 28% (2$^{nd}$ step) yields from 4-tert-pentylcatechol according to the typical procedure described for 1-(5-propyl-1,3-benzodioxol-2-yl)-1-ethanone.
¹H-NMR: 0.67 (t, J=7.3, 3H); 1.24 (s, 6H); 1.59 (q, J=7.3, 2H); 2.29 (s, 3H); 6.00 (s, 1H); 6.78 (d, J=8.1, 1H); 6.82 (dd, J=8.1, 1.8, 1H); 6.88 (d, J=1.8, 1H).
¹³C NMR: 9.1 (q), 24.1 (q), 28.7 (q), 28.7 (q), 37.0 (t), 37.9 (s), 106.6 (d), 107.1 (d), 107.9 (d), 119.4 (d), 144.3 (s), 144.5 (s), 146.7 (s), 200.5 (s). MS: 234 (6, M⁺), 191 (100), 162 (5), 134 (6), 105 (2), 77 (3), 43 (2).

1-(4-methyl-1,3-benzodioxol-2-yl)-1-ethanone

Obtained in 75% (1$^{st}$ step) and 30% (2$^{nd}$ step) yields from 3-methylcatechol according to the typical procedure described for 1-(5-propyl-1,3-benzodioxol-2-yl)-1-ethanone.
¹H-NMR: 2.25 (s, 3H); 2.28 (s, 3H); 6.00 (s, 1H); 6.68-6.73 (m, 2H); 6.76 (d, J=7.6, 1H).
¹³C NMR: 14.6 (q), 24.0 (q), 106.3 (d), 106.4 (d), 119.6 (s), 122.0 (d), 124.2 (d), 145.0 (s), 146.1 (s), 200.6 (s).

1-(5-Methyl-1,3-benzodioxol-2-yl)-1-ethanone

Obtained in 30% (1$^{st}$ step) and 55% (2$^{nd}$ step) yields from 4-methylcatechol according to the typical procedure described for 1-(5-propyl-1,3-benzodioxol-2-yl)-1-ethanone.
¹H-NMR: 2.27 (s, 3H); 2.28 (s, 3H); 5.99 (s, 1H); 6.66 (d, J=7.8, 1H); 6.71 (s, 1H); 6.75 (d, J=7.8, 1H).
¹³C-NMR: 21.2 (q), 24.0 (q), 106.5 (d), 108.3 (d), 109.8 (d), 122.2 (d), 132.3 (s), 144.6 (s), 146.7 (s), 200.5 (d).

1-(5-cyclopentylbenzo[d][1,3]-dioxol-2-yl)ethanone

Obtained in 54% (1$^{st}$ step) and 5% (2$^{nd}$ step) yields from 4-cyclopentyl-catechol according to the typical procedure described for 1-(5-propyl-1,3-benzodioxol-2-yl)-1-ethanone.
¹H-NMR: 1.46-1.56 (m, 2H); 1.61-1.72 (m, 2H); 1.73-1.83 (m, 2H); 1.98-2 (m, 2H); 2.27 (s, 3H); 2.87-2.96 (m, 1H); 5.98 (s, 1H); 6.73 (dd, J=7.9, 1.7, 1H); 6.76 (d, J=7.9, 1H); 6.78 (d, J=1.7, 1H).

$^{13}$C-NMR: 24.0 (q), 25.4 (t, 2C), 34.7 (t), 34.8 (t), 45.7 (d), 106.6 (d), 107.8 (d), 108.2 (d), 120.5 (d), 141.3 (s), 144.6 (s), 146.8 (s), 200.5 (s).

1-(5-(3-methylbut-2-enyl)benzoid[d][1,3]-dioxol-2-yl)ethanone

Obtained in 44% (1$^{st}$ step) and 32% (2nd step) yields from 4-(3-methylbut-2-enyl)benzene-1,2-diol (see DE 102007055124) according to the typical procedure described for 1-(5-propyl-1,3-benzodioxol-2-yl)-1-ethanone.

$^{1}$H-NMR: 1.70 (s, 3H); 1.74 (s, 3H); 2.27 (s, 3H); 3.26 (d, J=7, 2H); 5.28 (m, 1H); 5.99 (s, 1H); 6.67 (d, J=7.6, 1H); 6.71 (s, 1H); 6.76 (d, J=7.6, 1H).

$^{13}$C-NMR: 17.8 (q), 24.0 (q), 25.7 (q), 34.0 (t), 106.6 (d), 108.4 (d), 109.1 (d), 121.6 (d), 123.0 (d), 132.8 (s), 136.5 (s), 144.8 (s), 146.8 (s), 200.5 (s).

1-(4-methoxybenzoid[d][1,3]-dioxol-2-yl)ethanone

Obtained in 45% (1$^{st}$ step) and 32% (2$^{nd}$ step) yields from 3-methoxycatechol according to the typical procedure described for 1-(5-propyl-1,3-benzodioxol-2-yl)-1-ethanone.

$^{1}$H-NMR: 2.31 (s, 3H); 3.90 (s, 3H); 6.04 (s, 1H); 6.56 (d, J=8.2, 2H); 6.83 (t, J=8.2, 1H).

$^{13}$C-NMR: 24.0 (q), 56.6 (q), 102.4 (d), 106.9 (d), 108.1 (d), 122.8 (d), 134.5 (s), 144.1 (s), 148.0 (s), 199.9 (s).

1-(5-bromobenzoid[d][1,3]-dioxol-2-yl)ethanone

Obtained in 48% (1$^{st}$ step) and 24% (2nd step) yields from 4-bromocatechol according to the typical procedure described for 1-(5-propyl-1,3-benzodioxol-2-yl)-1-ethanone.

$^{1}$H-NMR: 2.30 (s, 3H); 6.07 (s, 1H); 6.75 (d, J=8, 1H); 6.99-7.02 (m, 2H).

$^{13}$C-NMR: 24.1 (q), 107.2 (d), 109.9 (d), 112.6 (d), 113.9 (s), 125.1 (d), 146.2 (s), 147.7 (s), 199.5 (s). MS: 244 (11, M$^+$), 242 (12, M$^+$), 201 (99), 199 (100), 145 (10), 143 (11), 120 (10), 92 (7), 79 (3), 64 (6), 63 (21), 62 (8), 53 (6), 43 (11).

1-(5-(pent-1-ynyl)benzoid[d][1,3]-dioxol-2-yl)ethanone

A solution of 1-(5-bromobenzo[d][1,3]dioxol-2-yl)ethanone (4.13 g), copper (I) iodide (0.16 g), pent-1-yne (2.32 g), triphenylphosphine palladium chloride (1.19 g) and triethylamine (7 ml) in acetonitrile (40 ml) was stirred overnight at 50° C. Then 100 ml of heptane were added and the organic layer was washed successively with a 2M HCl solution and three times with water, dried over MgSO$_4$ and concentrated. The crude reaction mixture was purified by flash chromatography on silica gel (eluant heptane/ethyl acetate 97/3) to give 3.91 g (22%) of a colorless oil.

$^{1}$H-NMR: 1.03 (t, J=7, 3H); 1.61 (tq, J=7, 7, 2H); 2.27 (s, 3H); 2.35 (t, J=7, 2H); 6.02 (s, 1H); 6.78 (d, J=8, 1H); 6.91 (d, J=2, 1H); 6.96 (dd, J=8, 2, 1H).

$^{13}$C-NMR: 13.5 (q), 21.3 (t), 22.2 (t), 24.0 (q), 80.1 (s), 89.1 (s), 106.8 (d), 108.6 (d), 112.0 (d), 118.3 (s), 126.4 (d), 146.3 (s), 146.6 (s), 199.7 (s).

1-(5-(cyclopentylmethyl)benzoid[d][1,3]-dioxol-2-yl)ethanone

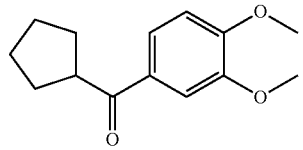 [SMILES: COc1ccc(C(=O)C2CCCC2)cc1OC]

Step a): Cyclopentyl(3,4-dimethoxyphenyl)methanone

To polyphosphoric acid (76 g) was added 1,2-dimethoxybenzene (7.9 g, 0.057 mol) followed by cyclopentanecarboxylic acid (9.8 g, 0.086 mol). The mixture was stirred at 60° C. during 24 hours then cooled down to −5° C. and quenched by the addition of 200 ml ice/water followed by 100 ml of ether. After stirring at room temperature for 3 hours, the two layers were separated and the aqueous phase extracted with three 100 ml portions of ether. The two ethereal phases were combined, washed with 50 ml of NaOH and 50 ml of brine and dried over MgSO$_4$. Filtration and concentration gave 15.5 g of dark brown oil. This oil was purified by vacuum distillation (180-190° C., 0.03 mbar) through a short path to give 11.8 g (88%) of a white solid.

$^{1}$H-NMR: 1.61-1.79 (m, 4H); 1.88-1.94 (m, 4H); 3.69 (quint., J=7.9, 1H); 3.93 (s, 3H); 3.95 (s, 3H); 6.89 (d, J=8.3, 1H); 7.52-7.62 (m, 2H).

$^{13}$C-NMR: 26.4 (t), 30.3 (t), 45.9 (d), 56.0 (q), 56.1 (q), 110.0 (d), 110.7 (d), 122.9 (d), 130.2 (s), 149.0 (s), 153.0 (s), 201.5 (s).

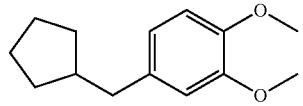 [SMILES: COc1ccc(CC2CCCC2)cc1OC]

Step b): 4-(cyclopentylmethyl)-1,2-dimethoxybenzene

A suspension of cyclopentyl(3,4-dimethoxyphenyl) methanone (10.8 g, 0.046 mol), wet Pd/C (1 g) in 10 ml of acetic acid and 10 ml of ethyl acetate was put in an autoclave at 60° C. with 20 bars of hydrogen during 24 hours. Filtration over Celite® and concentration gave 10 g of pale brown oil. This oil was purified by vacuum distillation (100-120° C., 0.02 mbar) through a short path to give 7.1 g (70%) of a colorless liquid.

$^{1}$H-NMR: 1.15-1.25 (m, 4H); 1.50-1.75 (m, 4H); 2.55 (d, J=7.4, 2H); 3.85 (s, 3H); 3.87 (s, 3H); 6.68-6.72 (m, 2H); 6.76-6.79 (m, 1H).

$^{13}$C-NMR: 25.0 (t), 32.5 (t), 41.7 (t), 42.1 (d), 55.8 (q), 55.9 (q), 111.0 (d), 112.1 (d), 120.6 (d), 135.1 (s), 147.0 (s), 148.7 (s).

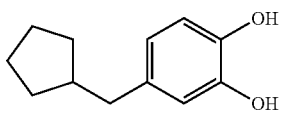 [SMILES: Oc1ccc(CC2CCCC2)cc1O]

Step c): 4-(cyclopentylmethyl)benzene-1,2-diol

A solution 4-(cyclopentylmethyl)-1,2-dimethoxybenzene (7.1 g, 0.032 mol) in 43 ml of hydrobromic acid (48% in water) and 4 ml of acetic acid was heated at 120° C. during 24 hours. The reaction mixture was cooled to room temperature and quenched with 50 ml of NH$_4$Cl solution. The aqueous phase extracted with three 100 ml portions of ether. The ethereal phase was washed with 50 ml of brine and dried over MgSO$_4$. Filtration and concentration gave 6.0 g (97%) of a brownish solid.

$^1$H-NMR: 1.10-1.18 (m, 2H); 1.46-1.54 (m, 2H); 1.56-1.71 (m, 4H); 1.95-2.05 (m, 1H); 2.47 (d, J=7.4, 2H); 5.54-5.71 (bs, 2H); 6.58 (dd, J=2.0, 8.1, 1H); 6.69 (d, J=2.0, 1H); 6.75 (d, J=8.1, 1H).

$^{13}$C-NMR: 24.9 (t), 32.4 (t), 41.4 (t), 42.0 (d), 115.2 (d), 115.9 (d), 121.2 (d), 135.8 (s), 141.2 (s), 143.3 (s).

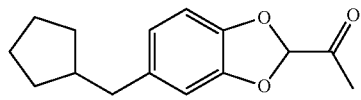

Step d): 1-(5-(cyclopentylmethyl)benzo[d][1,3]dioxol-2-yl)ethanone

Obtained in 40% (1$^{st}$ step) and 35% (2$^{nd}$ step) yields from 4-(cyclopentylmethyl)benzene-1,2-diol according to the typical procedure described for 1-(5-propyl-1,3-benzodioxol-2-yl)-1-ethanone.

$^1$H-NMR: 1.12-1.22 (m, 4H), 1.52-163 (m, 4H), 1.96-2.08 (m, 1H), 2.29 (s, 3H), 2.53 (d, J=8.2, 1H), 5.99 (s, 1H), 6.66 (dd, J=1.6, 7.9, 1H); 6.71 (d, J=1.5, 1 H); 6.76 (d, J=7.9, 1H).

$^{13}$C-NMR: 24.1 (q), 24.9 (t), 32.3 (t), 32.4 (t), 42.1 (d), 106.6 (d), 108.2 (d), 109.4 (d), 122.1 (d), 137.1 (s), 144.6 (s), 146.6 (s), 200.5 (s).

1-(5-(prop-1-enyl)benzoid[d][1,3]-dioxol-2-yl)ethanone 3.4 g of 1-(5-allylbenzo[d][1,3]dioxol-2-yl)ethanone and 68 mg (1 mol %) of ruthenium (III) acetylacetonate in 20 ml of o-xylene were stirred 2 days at 130° C., then cooled to room temperature. After concentration of the solvent in vacuum, the crude product was purified by flash chromatography on silica gel to give 1.3 g (38%) of a colorless oil.

$^1$H-NMR: 1.85 (dd, J=7, 1.6, 3H); 2.27 (s, 3H); 6.01 (s, 1H); 6.02-6.12 (dq, J=15.8, 6.6, 1H); 6.30 (dq, J=15.8, 1.6, 1H); 6.78 (m, 2H); 6.92 (s, 1H).

$^{13}$C-NMR: 18.3 (q), 24.0 (q), 105.6 (d), 106.7 (d), 108.5 (d), 120.6 (d), 124.6 (d), 130.3 (d), 133.2 (s), 145.7 (s), 147.2 (s), 200.1 (s).

1-(4-allylbenzo[d][1,3]-dioxol-2-yl)ethanone

Obtained in 51% (1$^{st}$ step) and 37% (2$^{nd}$ step) yields from 3-(allyl)-catechol according to the typical procedure described for 1-(5-propyl-1,3-benzodioxol-2-yl)-1-ethanone.

$^1$H-NMR: 2.27 (s, 3H); 3.36 (d, J=7, 2H); 5.07 (m, 1H); 5.10 (m, 1H); 5.90-6.01 (s, 1H); 6.02 (s, 1H); 6.72 (d, J=8, 1H); 6.75 (dd, J=8, 1.3, 1H); 6.81 (dd, J=8, 8, 1H).

$^{13}$C-NMR: 24.0 (q), 33.5 (t), 106.4 (d), 107.0 (d), 116.2 (t), 121.8 (s), 122.2 (d), 123.2 (d), 135.4 (d), 144.7 (s), 146.4 (s), 200.4 (s).

1-(5-(hex-2-enyl)benzoid[d][1,3]-dioxol-2-yl)ethanone

A solution of 1-(5-allylbenzo[d][1,3]dioxol-2-yl)ethanone (5 g), phenylmethylenebis(tricyclohexylphosphine) ruthenium dichloride (0.9 g) and pent-1-ene (5 g) in dichloromethane (40 ml) was stirred at room temperature. After 2 hours, a control by gc analysis shows 60% conversion, but three additional portions of 5 g of pent-1-ene were added during the reaction time (48 hours) to go to completion. Then, the reaction mixture was filtered on a short column of silica gel and concentrated in vacuum to remove the solvent. Finely the crude product was purified by flash chromatography on silica gel (eluant heptane/ethyl acetate 95/5) to give 0.8 g (19%) of a colorless oil, identified as a 85/15 E/Z mixture.

NMR spectra for the E isomer:

$^1$H-NMR: 0.90 (t, J=8, 3H); 1.40 (m, 2H); 2.00 (m, 2H); 2.28 (s, 3H); 3.25 (d, J=5, 2H); 5.50 (m, 2H); 6.00 (s, 1H); 6.68 (d, J=8, 1H); 6.73 (s, 1H); 6.77 (d, J=8, 1H).

$^{13}$C-NMR: 13.7 (q), 22.6 (t), 24.1 (q), 34.6 (t), 38.7 (t), 106.6 (d), 108.4 (d), 109.2 (d), 121.8 (d), 128.7 (d), 132.2 (d), 135.8 (s), 144.9 (s), 146.8 (s), 200.4 (s).

Example 2

Preparation of a Perfuming Composition

A perfuming composition for Eau de cologne for woman was prepared by admixing the following ingredients:

| Ingredient | Parts by weight |
| --- | --- |
| Isobornyl acetate | 10 |
| Benzyl acetate | 20 |
| Hexylcinnamic aldehyde | 10 |
| 10%* Allyl Amyl Glycolate | 12 |
| 10%* Ambrox ®$^{1)}$ | 10 |
| Bergamote essential oil | 30 |
| Citral | 1 |
| Coumarine | 2 |
| Cis-2-pentyl-1-cyclopentanol | 8 |
| Dihydromyrcenol | 40 |
| Eugenol | 24 |
| Exaltolide ®$^{2)}$ | 20 |
| 10%* Farenal ®$^{3)}$ | 10 |
| (1-ethoxyethoxy)cyclododecane | 20 |
| Florol ®$^{4)}$ | 10 |
| 70%** Galaxolide ®$^{5)}$ | 56 |
| Galbanum essential oil | 2 |
| 60%* Geraniol | 20 |
| Hedione ®$^{6)}$ HC | 24 |
| 3-(1,3-Benzodioxol-5-yl)-2-methylpropanal | 80 |
| Hivernal ®$^{7)}$ | 4 |
| Iso E ®$^{8)}$ Super | 40 |
| 10%* Isobutylquinoleine | 2 |
| Lilial ®$^{9)}$ | 20 |
| Linalol | 25 |
| Lyral ®$^{10)}$ | 16 |
| Mandarine essential oil | 8 |
| Cristal moss | 10 |
| Musc Ketone | 4 |
| Muscenone$^{11)}$ Delta | 16 |
| 10%* Methyl 2-nonynoate | 2 |
| Phenethylol | 18 |
| 10%* Cis-3-hexenol | 1 |

-continued

| Ingredient | Parts by weight |
|---|---|
| 1%* Para-cresol | 8 |
| Orange essential oil | 16 |
| Isobutyl salicylate | 6 |
| Benzyl salicylate | 240 |
| Sandela ®[12] | 30 |
| Sclareolate ®[13] | 50 |
| 2,4-Dimethyl-3-cyclohexene-1-carbaldehyde | 1 |
| 10%* Gamma undecalactone | 10 |
| 10%* Vanilline | 4 |
| (2,2-Dimethoxyethyl)benzene | 6 |
| Vertofix ®[13] Coeur | 54 |
| | 1000 |

*in dipropyleneglycol
**in isopropyle myristate
[1] (−)-(8R)-8,12-epoxy-13,14,15,16-tetranorlabdane; origin: Firmenich SA, Geneva, Switzerland
[2] pentadecanolide; origin: Firmenich SA, Geneva, Switzerland
[3] 2,6,10-trimethyl-9-undecenal; origin: Symrise, Germany
[4] tetrahydro-2-isobutyl-4-methyl-4(2H)-pyranol; origin: Firmenich SA, Geneva, Switzerland
[5] 1,3,4,6,7,8-hexahydro-4,6,6,7,8,8-hexamethyl-cyclopenta-g-2-benzopyrane; origin: International Flavors & Fragrances, USA
[6] methyl cis-dihydrojasmonate; origin: Firmenich SA, Geneva, Switzerland
[7] 3-(3,3/1,1-dimethyl-5-indanyl)propanal; origin: Firmenich SA, Geneva, Switzerland
[8] 1-(octahydro-2,3,8,8-tetramethyl-2-naphtalenyl)-1-ethanone; origin: International Flavors & Fragrances, USA
[9] 3-(4-tert-butylphenyl)-2-methylpropanal; origin: Givaudan SA, Vernier, Switzerland
[10] 4/3-(4-hydroxy-4-methylpentyl)-3-cyclohexene-1-carbaldehyde; origin: International Flavors & Fragrances, USA
[11] 3-methyl-(4/5)-cyclopentadecenone; origin: Firmenich SA, Geneva, Switzerland
[12] 5-(2,2,3-Trimethyl-3-cyclopentenyl)-3-methylpentan-2-ol; origin: Givaudan SA, Vernier, Switzerland
[13] propyl (S)-2-(1,1-dimethylpropoxy)propanoate; origin: Firmenich SA, Geneva, Switzerland
[14] methyl cedryl ketone; origin: Givaudan SA, Vernier, Switzerland The addition of 20 parts by weight of 1-(5-propyl-1,3-benzodioxol-2-yl)-1-ethanone to the above-described composition imparted to the latter a nice floral, watery aspect, while the addition of the 7-propyl-2H,4H-1,5-benzodioxepin-3-one provided only a watery effect.

The addition of 20 parts by weight of 1-(5-pentylbenzo[d][1,3]-dioxol-2-yl)ethanone to the above-described composition imparted to the latter an oriental connotation with its ozonic, balsamic notes.

The addition of 20 parts by weight of 1-(5-isopropylbenzo[d][1,3]dioxol-2-yl)ethanone to the above-described composition imparted to the latter a connotation more powdery/anisic as well as a watery note.

The addition of 20 parts by weight of 1-(5-butylbenzo[d][1,3]dioxol-2-yl)ethanone provided a similar effect than the addition of 1-(5-pentylbenzo[d][1,3]-dioxol-2-yl)ethanone.

The addition of 20 parts by weight of 1-(5-cyclopentyl-benzo[d][1,3]dioxol-2-yl)ethanone imparted a peachy/ozonic note and exalted the citrus notes of the original fragrance.

Example 3

Preparation of a Perfuming Composition

A perfuming composition for Eau de cologne for man was prepared by admixing the following ingredients:

| Ingredient | Parts by weight |
|---|---|
| Vetyveryl acetate | 130 |
| Aladinate ®[1] | 5 |
| 10%* Aldehyde C 12 | 10 |
| 10%* Aldehyde MNA | 15 |
| Ambrox ®[2] | 70 |
| 10%* Methyl anthranilate | 20 |

-continued

| Ingredient | Parts by weight |
|---|---|
| Bergamote essential oil | 450 |
| Cardamome essential oil | 5 |
| Cashmeran ®[3] | 35 |
| Lemon essential oil | 100 |
| Citronellol | 50 |
| Coumarine | 60 |
| Dihydromyrcenol | 600 |
| Elemi essential oil | 20 |
| Sweet fennel essential oil | 70 |
| 2-Methyl-4-(2,2,3-trimethyl-3-cyclopenten-1-yl)-4-penten-1-ol | 25 |
| Guaiacum essential oil | 20 |
| 10%* Gamma Decalactone | 25 |
| Geranium essential oil | 10 |
| Habanolide ®[4] | 250 |
| Hedione ®[5] HC | 100 |
| Helvetolide ®[6] | 50 |
| 1%* 1-Phenylvinyl acetate[7] | 25 |
| Iralia ®[8] | 100 |
| Iso E ®[9] Super | 600 |
| 10%* Isobutylquinoleine | 30 |
| Lilial ®[10] | 250 |
| Nutmeg essential oil | 20 |
| Muscenone[11] Delta | 50 |
| Trans-1-(2,2,6-trimethyl-1-cyclohexyl)-3-hexanol[8] | 50 |
| Polysantol ®[12] | 20 |
| Rose essential oil | 10 |
| Amyle salicylate | 40 |
| Cis-3-hexenol salicylate | 160 |
| Trimofix ®[13] | 90 |
| 10%* 2,4-Dimethyl-3-cyclohexene-1-carbaldehyde | 25 |
| Undecavertol ®[14] | 25 |
| Vanilline | 160 |
| 10%* 8,13:13,20-diepoxy-15,16-dinorlabdane | 25 |
| | 3800 |

*in dipropyleneglycol
**in isopropyle myristate
[1] (Z)-3-methyl-2-hexenyl acetate; origin: Firmenich SA, Geneva, Switzerland
[2] (−)-(8R)-8,12-epoxy-13,14,15,16-tetranorlabdane; origin: Firmenich SA, Geneva, Switzerland
[3] 1,2,3,5,6,7-hexahydro-1,1,2,3,3-pentamethyl-4-indenone; origin: International Flavors & Fragrances, USA
[4] pentadecenolide; origin: Firmenich SA, Geneva, Switzerland
[5] methyl cis-dihydrojasmonate; origin: Firmenich SA, Geneva, Switzerland
[6] (1S,1'R)-2-[1-(3',3'-dimethyl-1'-cyclohexyl)ethoxy]-2-methylpropyl propanoate; origin: Firmenich SA, Geneva, Switzerland
[7] origin: Firmenich SA, Geneva, Switzerland
[8] mixture of methylionones isomers; origin: Firmenich SA, Geneva, Switzerland
[9] 1-(octahydro-2,3,8,8-tetramethyl-2-naphtalenyl)-1-ethanone; origin: International Flavors & Fragrances, USA
[10] 4/3-(4-hydroxy-4-methylpentyl)-3-cyclohexene-1-carbaldehyde; origin: International Flavors & Fragrances, USA
[11] 3-methyl-(4/5)-cyclopentadecenone; origin: Firmenich SA, Geneva, Switzerland
[12] 3,3-dimethyl-5-(2,2,3-trimethyl-3-cyclopenten-1-yl)-4-penten-2-ol; origin: Firmenich SA, Geneva, Switzerland
[13] 1-(2,6,10-Trimethyl-1(2),5,9-cyclododecatrien-1-yl)-1-ethanone; origin: International Flavors & Fragrances, USA
[14] 4-methyl-3-decen-5-ol; origin: Givaudan SA, Vernier, Switzerland The addition of 50 parts by weight of 1-(5-propyl-1,3-benzodioxol-2-yl)-1-ethanone to the above-described composition imparted to the latter a watery freshness as well as a nice floral touch rendering the composition more sparkling.

The addition of 50 parts by weight of 1-(5-pentylbenzo[d][1,3]-dioxol-2-yl)ethanone to the above-described composition imparted to the latter a watery note and reinforced the coumarine notes.

The addition of 50 parts by weight of 1-(5-isopropylbenzo[d][1,3]-dioxol-2-yl)ethanone to the above-described composition imparted to the latter a reinforced floral aspect but very fresh and watery.

The addition of 50 parts by weight of 1-(5-cyclopentyl-benzo[d][1,3]-dioxol-2-yl)ethanone imparted a feminine twist by providing its typical peachy/ozonic note.

What is claimed is:

1. A method to confer, enhance, improve or modify the odor properties of a perfuming composition or of a perfumed article, which method comprises adding to said composition or article an effective amount of at least a compound of formula

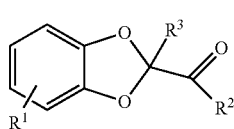

in the form of any one of its stereoisomers or a mixture thereof, and wherein $R^1$ independently represents a substituent of the benzene ring and is a halogen atom or a linear, branched or cyclic $C_{1-8}$ alkyl, alkenyl, alkynyl, alkoxy or alkenyloxy group;
$R^2$ represents a $C_{1-3}$ alkyl group; and
$R^3$ represents a hydrogen atom or a methyl or ethyl group.

2. A method according to claim 1 wherein said compound (I) is of formula

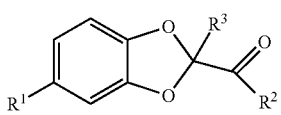

wherein $R^1$, $R^2$ and $R^3$ are as defined in claim 1.

3. A method according to claim 2 wherein said $R^1$ independently represents a substituent of the benzene ring and is a linear or branched $C_{1-6}$alkyl, alkenyl, alkynyl or alkoxy group or represents a $C_{5-6}$ cyclic alkyl, alkenyl or methylcyloalkyl group.

4. A method according to claim 3 wherein $R^1$ independently represents a substituent of the benzene ring and is a bromine atom or a linear, branched or cyclic $C_{1-6}$ alkyl, alkenyl, alkynyl, alkoxy or alkenyloxy group.

5. A method according to claim 4 wherein said $R^1$ independently represents a substituent of the benzene ring and is a linear or branched $C_{1-6}$ alkyl or alkenyl group.

6. A method according to claim 2 wherein said $R^3$ represents a hydrogen atom or a methyl group.

7. A method according to claim 1 wherein said $R^1$ independently represents a substituent of the benzene ring and is a linear or branched $C_{1-6}$ alkyl, alkenyl, alkynyl or alkoxy group or represents a $C_{5-6}$ cyclic alkyl, alkenyl or methylcyloalkyl group.

8. A method according to claim 7 wherein $R^1$ independently represents a substituent of the benzene ring and is a bromine atom or a linear, branched or cyclic $C_{1-6}$ alkyl, alkenyl, alkynyl, alkoxy or alkenyloxy group.

9. A method according to claim 8 wherein said $R^1$ independently represents a substituent of the benzene ring and is a linear or branched $C_{1-6}$ alkyl or alkenyl group.

10. A method according to claim 1 wherein said $R^2$ represents a methyl or ethyl group.

11. A method to confer, enhance, improve or modify the odor properties of a perfuming composition or of a perfumed article, which method comprises adding to said composition or article an effective amount of a compound of Formula (I) selected from the group consisting of 1-(5-isopropylbenzo[d][1,3]dioxol-2-yl)ethanone, 1-(5-propyl-1,3-benzodioxol-2-yl)-1-ethanone, 1-(5-pentylbenzo[d][1,3]-dioxol-2-yl)ethanone, 1-(2-methyl-5-propylbenzo[d][1,3]-dioxol-2-yl)ethanone, 1-(5-butylbenzo[d][1,3]dioxol-2-yl)ethanone, 1-(5-hexylbenzo[d][1,3]dioxol-2-yl)ethanone, 1-(5-tert-pentylbenzo[d][1,3]-dioxol-2-yl)ethanone, 1-(5-tert-butyl-1,3-benzodioxol-2-yl)-ethanone, 1-(5-cyclopentylbenzo[d][1,3]dioxol-2-yl)ethanone, 1-(5-(3-methylbut-2-enyl)benzo[d][1,3]dioxol-2-yl)ethanone, 1-(5-(cyclopentylmethyl)benzo[d][1,3]-dioxol-2-yl)ethanone, (E)-1-(5-(prop-1-enyl)benzo[d][1,3]-dioxol-2-yl)ethanone, (E/Z)-1-(5-(hex-2-enyl)benzo[d][1,3]dioxol-2-yl)ethanone and 1-(4-methyl-1,3-benzodioxol-2-yl)-1-ethanone.

12. A method according to claim 11, wherein said compound is selected from the group consisting of 1-(5-isopropylbenzo[d][1,3]dioxol-2-yl)ethanone, 1-(5-propyl-1,3-benzodioxol-2-yl)-1-ethanone, 1-(5-pentylbenzo[d][1,3]dioxo-2-yl)ethanone, 1-(2-methyl-5-propylbenzo[d][1,3]dioxol-2-yl)ethanone, (E)-1-(5-(prop-1-enyl)benzo[d][1,3]dioxol-2-yl)ethanone, (E/Z)-1-(5-(hex-2-enyl)benzo[d][1,3]dioxol-2-yl)ethanone and 1-(5-butylbenzo[d][1,3]-dioxol-2-yl)ethanone.

13. A method according to claim 1 or 11 wherein the compound is added to a perfumed article comprising a perfuming consumer product that includes a perfumery consumer base.

14. A method according to claim 13 wherein the perfumery consumer base is a perfume, a fabric care product, a body-care product, an air care product or a home care product.

15. A method according to claim 14 wherein the perfumery consumer is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

16. A method according to claim 1 or 11 wherein the compound is added to a perfuming composition comprising at least one ingredient selected from the group consisting of a perfumery carrier and a perfumery base; and optionally at least one perfumery adjuvant.

17. A method according to claim 16 wherein the perfumery base is a perfume, a fabric care product, a body-care product, an air care product or a home care product.

18. A method according to claim 17 wherein the perfumery base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

19. A method according to claim 1 or 11 wherein the compound to be added is of formula (I)

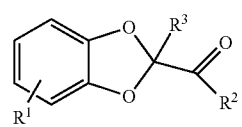

in the form of any one of its stereoisomers or a mixture thereof, and wherein $R^1$ independently represents a substituent of the benzene ring and is a halogen atom or a linear, branched or cyclic $C_{1-8}$alkyl, alkenyl, alkynyl, alkoxy or alkenyloxy group;

$R^2$ represents a $C_{1-3}$ alkyl group or —OH; and $R^3$ represents a hydrogen atom or a methyl or ethyl group;

provided that 1-[5-(1,1-dimethylethyl)-2-methyl-1,3-benzodioxol-2-yl]-ethanone, 1-(4-methoxy-2-methyl-1,3-benzodioxol-2-yl)-ethanone, 1-(5-methoxy-2-methyl-1,3-benzodioxol-2-yl)-ethanone-methoxy-1,3-benzodioxole-2-carboxylic acid, 5-methyl-1,3-benzodioxole-2-carboxylic acid and 4-methyl-1,3-benzodioxole-2-carboxylic are excluded.

* * * * *

UNITED STATES PATENT AND TRADEMARK OFFICE
CERTIFICATE OF CORRECTION

PATENT NO. : 8,987,188 B2
APPLICATION NO. : 13/876404
DATED : March 24, 2015
INVENTOR(S) : Huboux et al.

It is certified that error appears in the above-identified patent and that said Letters Patent is hereby corrected as shown below:

IN THE CLAIMS:

Column 23:
Line 36, delete "$C_{1-6}$alkyl" and insert -- $C_{1-6}$ alkyl --.

Column 24:
Line 1, delete "1-(5-pentylbenzo[d][1,3]-dioxol-2-yl)etha-" and insert
 -- 1-(5-pentylbenzo[d][1,3]dioxol-2-yl)etha- --.
Line 2, delete "1-(2-methyl-5-propylbenzo[d][1,3]-dioxol-2-yl)" and insert -- 1-(2-methyl-5-propylbenzo[d][1,3]dioxol-2-yl) --.
Line 6, delete "benzodioxol-2-yl)-ethanone," and insert -- benzodioxol-2-yl)-1-ethanone, --.
Line 9, delete "[1,3]-dioxol-2-yl)ethanone," and insert -- [1,3]dioxol-2-yl)ethanone, --.
Line 16, delete "1-(5-pentylbenzo[d][1,3]dioxo-" and insert -- 1-(5-pentylbenzo[d][1,3]dioxol- --. Line 20, delete "1-(5-butylbenzo[d][1,3]-dioxol-2-yl)" and insert -- 1-(5-butylbenzo[d][1,3]dioxol-2-yl) --.

Signed and Sealed this
Fourteenth Day of July, 2015

Michelle K. Lee
*Director of the United States Patent and Trademark Office*